United States Patent [19]

Imran et al.

[11] Patent Number: 5,662,608
[45] Date of Patent: Sep. 2, 1997

[54] LOW PROFILE BALLOON CATHETER AND METHOD

[75] Inventors: Mir A. Imran, Palo Alto; Deepak R. Gandhi, San Jose; Anant V. Hegde, Newark, all of Calif.

[73] Assignee: Intelliwire, Inc., Sunnyvale, Calif.

[21] Appl. No.: 507,655

[22] Filed: Jul. 26, 1995

[51] Int. Cl.$^6$ .................................................... A61M 29/00
[52] U.S. Cl. .............................. 604/96; 604/101; 606/192
[58] Field of Search ............................ 604/96–103, 21, 604/28; 606/192–197

[56] References Cited

U.S. PATENT DOCUMENTS

| | | |
|---|---|---|
| 4,958,634 | 9/1990 | Jang . |
| 5,242,396 | 9/1993 | Evard . |
| 5,304,132 | 4/1994 | Jang . |
| 5,328,472 | 7/1994 | Steinke et al. . |

*Primary Examiner*—Robert A. Hafer
*Assistant Examiner*—Perry E. Van Over
*Attorney, Agent, or Firm*—Flehr Hohbach Test Albritton & Herbert LLP

[57] ABSTRACT

A low profile catheter comprising a flexible elongate tubular member having proximal and distal extremities and having a guide wire lumen and at least one balloon inflation lumen extending from the proximal extremity to the distal extremity, said at least one balloon inflation lumen being offset eccentrically with respect to said guide wire lumen, the distal extremity of said flexible elongate tubular member having at least one inflatable balloon formed thereon and having an interior in communication with said at least one balloon inflation lumen, said guide wire lumen extending through said at least one inflatable balloon and being offset eccentrically with respect to said at least one inflatable balloon.

6 Claims, 3 Drawing Sheets

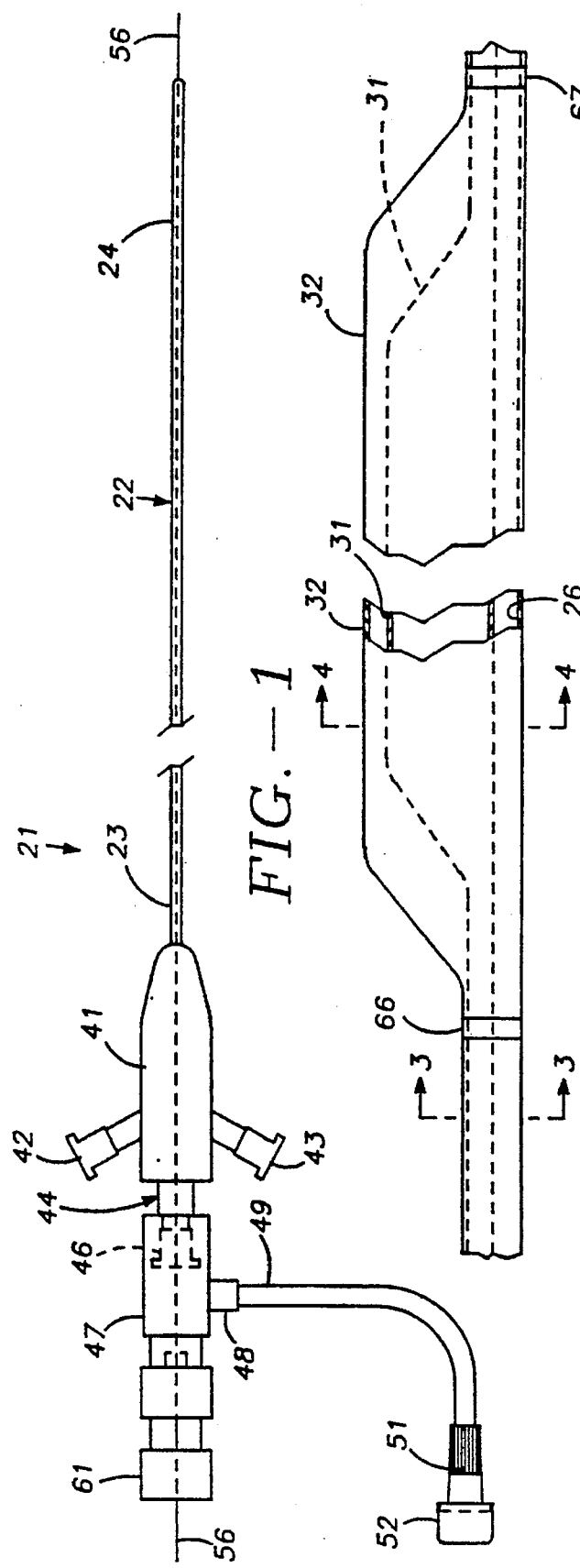
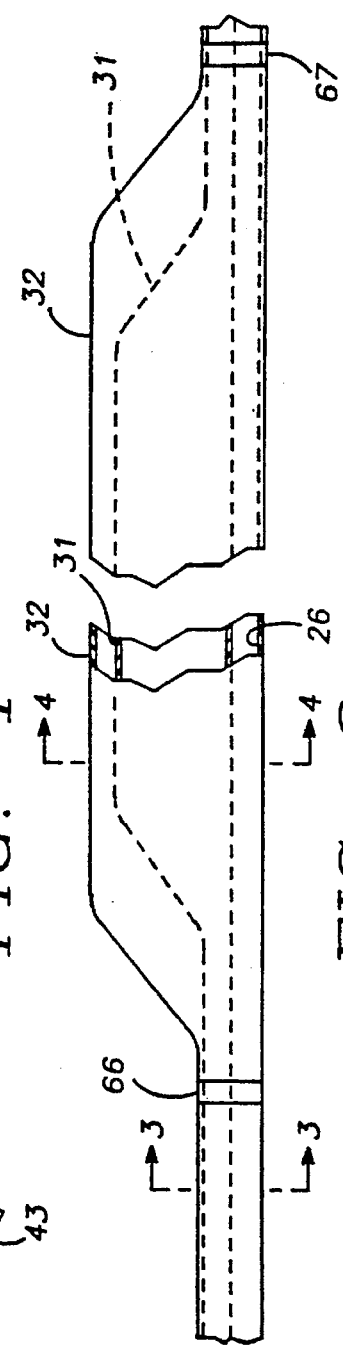
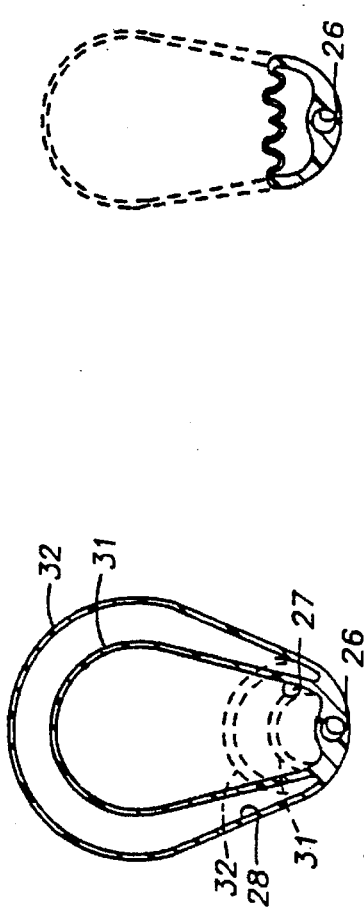
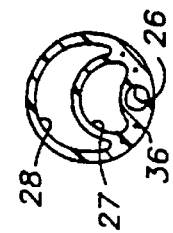

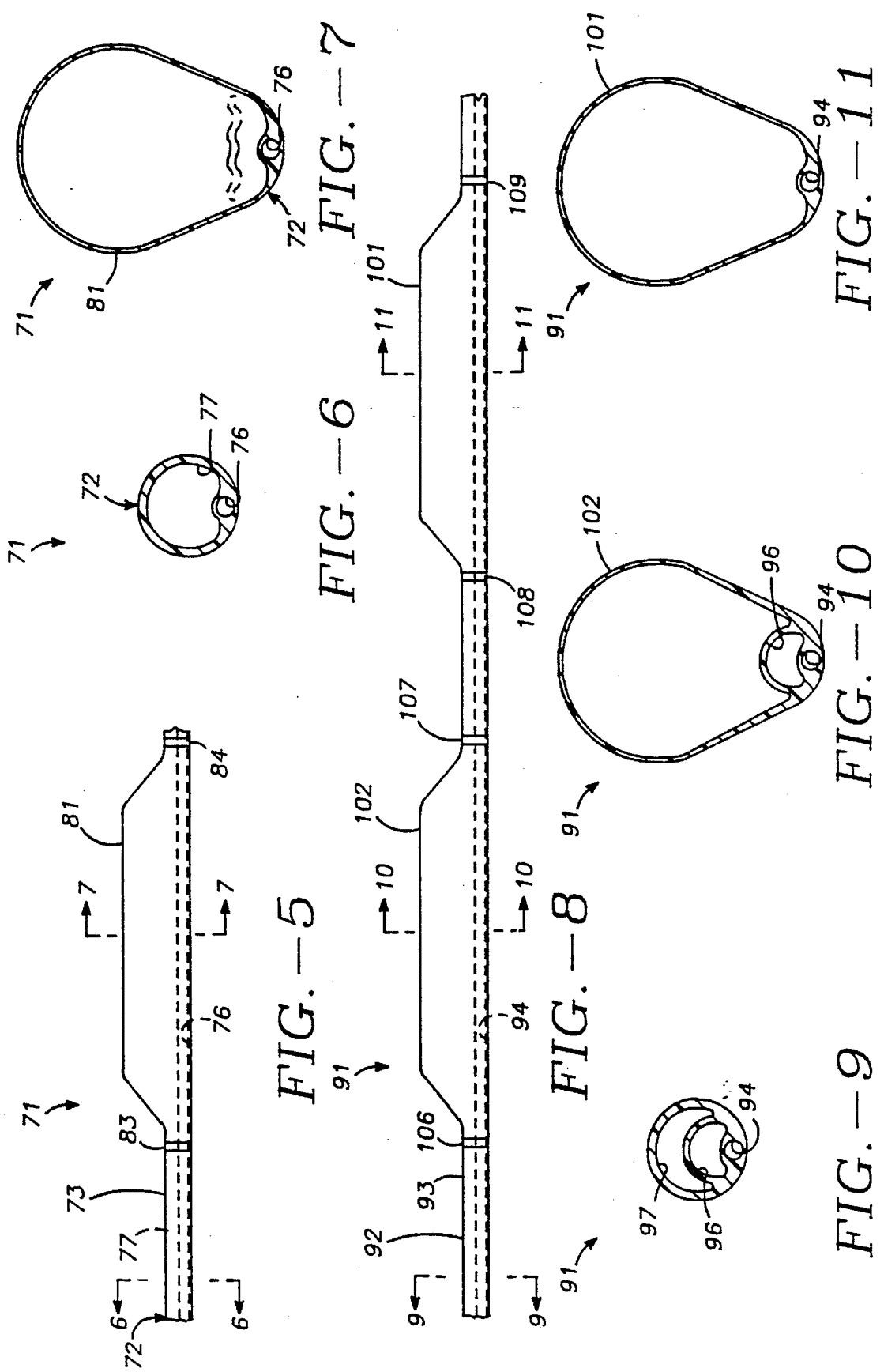

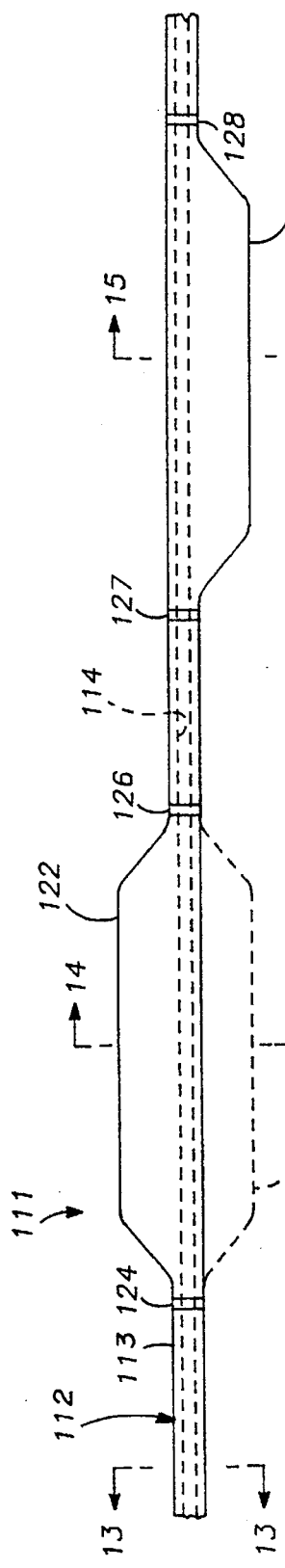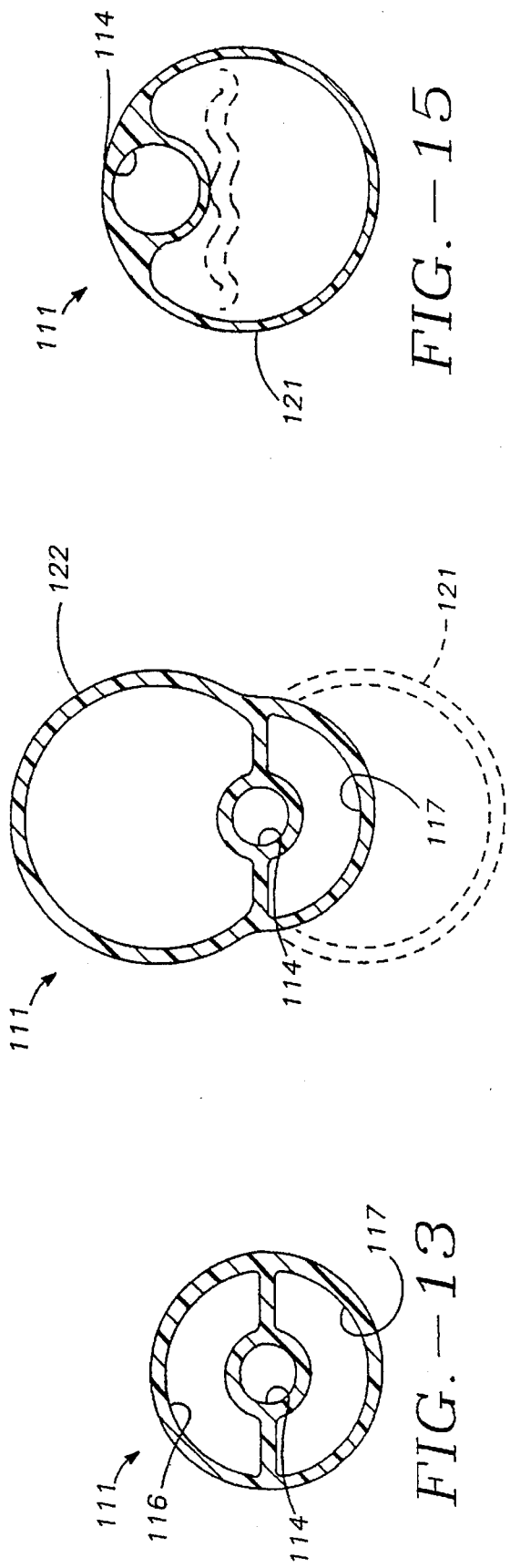

5,662,608

LOW PROFILE BALLOON CATHETER AND METHOD

This invention relates to a low profile balloon catheter and method and more particularly to a balloon catheter and method which utilizes a unitary construction.

Balloon catheters have heretofore provided, it has been conventional to provide such balloon catheters with balloons which are concentric with the shaft of the catheter so that the balloon inflates uniformly about the axis of the shaft of the catheter to a diameter which is normally substantially greater than the diameter shaft of the catheter. When the balloon is deflated, it typically has a circumference which is usually greater than the circumference of the shaft so that there is an excess of a balloon material which tends to fold up in various manners about the circumference of the shaft. This provides an overall circumference which is substantially greater than the circumference of the shaft making it difficult to maintain a low profile to make it difficult to negotiate the distal extremity of the balloon catheter through small vessels and into small stenoses. There is therefore need for new and improved balloon catheter and a method which makes it possible to overcome these disadvantages.

In general, it is an object of the present invention to provide a balloon catheter and method which makes it possible to achieve a very low profile for the balloon which is essentially the same as that of the shaft.

Another object of the invention is to provide a balloon catheter and method of the above character in which single and multiple balloons can be provided.

Another object of the invention is to provide a catheter and method of the above character in which the multiple balloons can be eccentric.

Another object of the invention is to provide a balloon catheter and method of the above character in which the guide wire lumen is provided on one side of the shaft.

Another object of the invention is to provide a balloon catheter and method of the above character in which the balloons are eccentrically disposed on the distal extremity of the catheter shaft.

Another object of the invention is to provide a balloon catheter and method of the above character in which the balloons are eccentrically inflated with respect to the catheter shaft and with respect to the other balloons.

Another object of the invention is to provide a balloon catheter and method in which the multiple balloons can be inflated eccentrically in staggered positions.

Another object of the invention is to provide a balloon catheter and method of the above character in which the balloons can be inflated in offset eccentric positions.

Another object of the invention is to provide a balloon catheter and method of the above character in which rapid exchange capabilities are provided.

Additional objects and features of the invention will appear from the following description in which the preferred embodiments are set forth in detail in conjunction with the accompanying drawing.

FIG. 1 is a side elevational view of a balloon catheter incorporating the present invention.

FIG. 2 is an enlarged view partially in section of the distal extremity of the balloon catheter shown in FIG. 1.

FIG. 3 is a cross-sectional view taken along the line 3—3 of FIG. 2.

FIG. 4 is a cross-sectional view taken along the line 4—4 of FIG. 2.

FIG. 4A is a view similar to FIG. 4 but showing the deflated balloon profile.

FIG. 5 is an enlarged view of the distal extremity of a catheter incorporating the present invention in which a single balloon has been provided.

FIG. 6 is a cross-sectional view taken along the line 6—6 of FIG. 5.

FIG. 7 is a cross-sectional view taken along the line 7—7 of FIG. 5. Dotted lines show the deflated balloon profile.

FIG. 8 is an enlarged side elevational view of the distal extremity of a balloon catheter incorporating the present invention in which the balloons are staggered.

FIG. 9 is a cross-sectional view taken along the line 9—9 of FIG. 8.

FIG. 10 is a cross-sectional view taken along the line 10—10 of FIG. 8.

FIG. 11 is a cross-sectional view taken along the line 11—11 of FIG. 8.

FIG. 12 is an enlarged side elevational view of the distal extremity of another embodiment of the balloon catheter incorporating the present invention in which the balloons are offset on opposite sides.

FIG. 13 is a cross-sectional view taken along the-line 13—13 of FIG. 12.

FIG. 14 is a cross-sectional view taken along the line 14—14 of FIG. 12.

FIG. 15 is a cross-sectional view taken along the line 15—15 of FIG. 12 and showing in dotted lines the deflated profile of the distal balloon.

In general, the low profile balloon catheter of the present invention comprises a flexible elongate tubular member which has proximal and distal extremities and has a guide wire lumen and at least one balloon inflation lumen extending from the proximal extremity to the distal extremity with said at least one balloon inflation lumen being offset eccentrically with respect to the guide wire lumen. The distal extremity of the flexible elongate tubular member has at least one inflatable balloon formed therein and having an interior in communication with the at least one balloon inflation lumen. The guide wire lumen extends through the balloon and is offset eccentrically with respect to the balloon.

More particular as shown in FIGS. 1 through 4 of the drawings, the low profile balloon catheter 21 consists of a flexible elongate tubular member 22 having proximal and distal extremities 23 and 24 and having a guide wire lumen 26 extending from the proximal extremity 23 to the distal extremity 24. It has at least one balloon inflation lumen and as shown in FIGS. 1–4, two balloon inflation lumens 27 and 28 which extend from the proximal extremity 23 to the distal extremity 24. The flexible elongate tubular member 22 is formed of a suitable thermoplastic material well known to those skilled in the art as for example high density polyethylene. The material should be one which can withstand high pressure as for example 15 atmospheres at a minimum.

At least one balloon and as shown in FIGS. 1–4, two balloons 31 and 32 are provided on the distal extremity 24 of the flexible elongate tubular member 22. Since the balloons 31 and 32 are typically formed of a non-elastomeric material, it is desirable that the balloons be formed of the same material as the flexible elongate tubular member 22 so that they can be formed therefrom and made integral therewith. It should however be appreciated in connection with the invention that thermoplastic elastomers can be utilized when elastomeric balloons are desired.

The plastic utilized in accordance with the present invention can be extruded in a conventional manner to provide the flexible elongate tubular member 22 with the guide wire lumen 26 and the balloon inflation lumens 27 and 28 therein.

After the flexible elongate tubular member 22 has been extruded, the distal extremity can be thinned down by the application of heat and by stretching the distal extremity to aide in keeping a low balloon profile in accordance with the present invention. Thereafter the balloons 31 and 32 are formed therein. This can be accomplished by placing a mandrel in the guide wire lumen 26 to maintain the desired size for a guide wire as for example one which can accept a 0.014" guide wire and such as an inside diameter of 0.016". With the mandrel therein, the distal extremity of the flexible elongate tubular member 22 can be heated and tension applied to the distal extremity. The distal extremity of the flexible elongate tubular member 22 can be closed off to seal the balloon inflation lumens 27 and 28. As can be seen in FIGS. 3 and 4, the balloon inflation lumens 27 and 28 are offset to one side of the flexible elongate tubular member 22 or in other words are offset from the center axis of the flexible elongate tubular member 22.

The distal extremity of the flexible elongate tubular member 22 in which the balloon or balloons is to be formed is placed in a mold of a suitable type as for example a glass mold (not shown) of a diameter and length suitable for the first or inner balloon 31 so that the balloon will be formed eccentrically with respect to the guide wire lumen 26. As soon as the mold is in place and the plastic has been heated to the desired temperature and placed under tension, a suitable fluid or air is introduced into the balloon inflation lumen 27 to supply air under pressure into the portion of the flexible elongate tubular member 22 within the mold to cause the plastic material to expand outwardly and thin out in an eccentric manner to form the first balloon 31 and carrying with it the plastic which is to form the second balloon 32. After the appropriate size balloon 31 has been formed in the mold, the air pressure within the balloon 31 is removed. Balloon 31 is taken out of the mold and permitted to cool down to room temperature. This cooling can be effected by supplying cooling air to the distal extremity 24. After the balloon 31 has been cooled,the distal extremity is then heated and placed under tension and place in another mold of the same type as hereinbefore described which is sized for formation of the second balloon 32. Air pressure is then supplied to the balloon inflation lumen 28 to cause the formation of the second balloon by causing the plastic forming the second balloon inflation lumen 22 to expand eccentrically and to thin out to form the larger size balloon 32. After the balloon 32 has been formed in the mold, the air pressure can be released and the mold permitted to cool permitting collapse of the balloon 32 In the manner shown in FIG. 4 so that the overall profile for the distal extremity carrying the balloons 31 and 32 is less than or substantially of the same circumference and diameter as the proximal extremity of the flexible elongate tubular member 22 and forming the shaft for the catheter 21. The inflated balloons 31 and 32 when expanded have an egg-shaped configuration in cross section as shown in FIG. 4.

By this procedure, the balloons can be formed with a wall thickness which is quite thin as for example from 0.0002" to 0.0010" and preferably a thickness of approximately 0.005" to 0.006" to form balloons of various desired diameters as can be seen from FIG. 4, the wall thickness of the balloons decrease in a direction away from the guide wire lumen 26. Thus by way of example, the balloons can have an exterior diameter of 1.5 millimeters up to 8.0 millimeters. Balloon 31 can have a diameter 2.5 millimeters and the balloon 32 a diameter of 3.5 millimeters. As shown in FIG. 4, the balloons 31 and 32 because of their thin walls collapse into a crescent-shape configuration as shown. By way of example, the catheter 21 can be of a suitable size as for example 3.0 French having an outside diameter of 0.039" with the guide wire lumen 56 being formed of a size so that it can accommodate a guide wire of 0.014" as hereinbefore described.

The distal extremity 24 with the balloons 31 and 32 thereon should have sufficient column strength to provide the necessary pushability for the balloon catheter and particularly because of he presence of the guide wire lumen 26 extending therethrough. However, in the event additional column strength to provide greater pushability is desired, a an elongate stiffener element such as wire 36 can then be placed in the outer crescent shaped portion of the distal extremity 24 in which the balloons 31 and 32 are formed as shown in FIG. 3 and embedded in the outer surface thereof. The braid thus provides additional column strength and pushability as well as improved torquability. It also should be appreciated that a similar braid 36 can be provided along the entire length of the flexible elongate tubular member 22 to provide additional torquability and pushability for the shaft of the catheter 21.

A balloon inflation manifold 41 is mounted on the proximal extremity 23 of the flexible elongate tubular member 22 and is formed of a suitable material such as plastic. First and second Luer fittings 42 and 43 are provided on opposite sides of the manifold 41, the first Luer fitting 42 being in communication with the first balloon inflation lumen 27 for the balloon 31 and the Luer fitting 43 being in communication with the second balloon inflation lumen 28 for the second balloon 32. The manifold 41 is also provided with a third Luer fitting 44 which is in axial alignment with the axial axis of the flexible elongate tubular member 22 and is in communication with the guide wire lumen 26. A male Luer fitting 46 is coupled to a female Luer fitting 47 of a conventional type and is provided with a side port 48 which is connected to flexible tubing 49. The flexible tubing 49 is connected to another Luer fitting 51 which is closed off by a removable cap 52. The tubing 49 is in communication with the guide wire lumen 26 so that a suitable liquid as for example a saline solution or a heparin solution can be introduced along with a guide wire 56 extending into and through the guide wire lumen 26. A conventional hemostasis valve 61 is mounted on the Luer fitting 47 and has a port (not shown) through which the guide wire 56 extends. The hemostasis valve 61 includes a sealing member (not shown) which can be pressed against the guide wire 56 to prevent the leaking of blood out around the guide wire 56 when the balloon catheter is placed in a vessel in a human body.

To aide in locating and positioning of the balloons 31 and 32 in medical procedures hereinafter described, it is desirable to provide radiopaque markers as for example radiopaque markers 66 and 67 formed on opposite ends of the balloons 31 and 32. As is well known to those skilled in the art, the radiopaque markers 66 and 67 can be formed by embedding radiopaque particles such as barium salt in convenient bands to form the radiopaque markers 66 and 67. Alternatively, metallic bands can encircle the flexible elongate tubular member and can be formed of a suitable radiopaque material such as platinum or a platinum tungsten alloy or gold.

Operation and use of the low profile balloon catheter 21 may now be briefly described as follows. Let it be assumed that it is desired to utilize the catheter 1 in a conventional angioplasty procedure in which there is a need to enlarge the flow passageway through stenosis in a vessel in the heart wall of he patient. Typically in such a procedure, a guiding catheter would be introduced through the femoral artery of the patient into close proximity to the desired location in the patient. Thereafter, a guide wire 56 is introduced into the guiding catheter and advanced through the stenosis in a conventional manner.

After the guide wire 56 has been positioned, the low profile dilatation catheter 21 can be threaded over the guide wire and advanced through the guiding catheter and into and through the stenosis so that the balloons 31 and 32 are in registration with the stenosis. Alternatively, the guide wire can be placed in the balloon catheter 21 prior to insertion of the guide wire into the vessel. When that is the case, the guide wire 56 and the balloon catheter 21 can be progressively advanced into the guiding catheter and into the stenosis. As soon as the balloons 31 and 32 are in place, the first balloon 31, i.e. the smaller balloon can be inflated by connecting an inflation device to the lower fitting 42 to inflate the balloon 31. The balloon 31 will be inflated into an egg-shaped profile off to one side of the guide wire lumen 26 to cause compression of the plaque forming the stenosis to create a larger size flow passage through the stenosis. While the smaller balloon 31 is being inflated, the larger balloon 32 is carried thereby in a deflated condition and moved into engagement with the plaque forming the stenosis to form a larger flow passage extending through the stenosis. The smaller balloon 31 can be inflated and deflated several times as desired by the physician.

After the inflation and deflation of the smaller balloon 31 for several period of times, it may be desired to provide a still larger flow passage. This can be readily accomplished without replacement of the balloon catheter 21 by merely supplying a balloon inflation medium to the second balloon inflation lumen 28 by connecting an inflation device to the Luer fitting 43 and causing expansion to a larger size as represented by the dotted line in FIG. 4 to still further compress the plaque and to form a still larger flow passage through the stenosis. During the time that the second balloon 32 is being inflated, the first balloon 31 can remain inflated or can remain deflated. The positioning of the balloons 31 and 32 in the stenosis in the catheter can be readily observed through use of the radiopaque marker 66 and 67.

After the desired size flow passage through the stenosis has been achieved, the balloons 31 and 32 can be deflated as shown in FIG. 4A and the balloon catheter 21 removed after which the guiding catheter can be removed and the site into the femoral artery sutured. From the foregoing, it can be seen that there has been provided a low profile balloon catheter 21 in which the collapsed balloon collapse into crescent-shaped forms which do not have a cross-sectional area which is substantially greater than the cross-sectional area of the catheter itself. For this reason and by use of this type of construction, it is possible to provide low profile balloon catheter 21 which can negotiate small vessels and pass through very small flow openings in stenoses in such vessels.

Since the low profile balloon catheter 21 can be formed of a single unitary piece of material, it is possible to manufacture such catheters relatively inexpensively. Even if the desired pushability and torquability is desired for such catheters, this increased pushability and torquability can be readily incorporated into the catheters merely by incorporating a braid in the appropriate locations along the length of the catheter.

Another embodiment of a low profile balloon catheter incorporating the present invention is the catheter 71 shown in FIG. 5, 6 and 7 and consists of a flexible elongate member 72 which only the distal extremity 73 is shown by having a guide wire lumen 76 offset to one side of the same and having a single balloon inflation lumen 77 eccentrically disposed with respect to the guide wire lumen 76. A balloon 81 is formed in the distal extremity in the same manner as which the balloon 31 and 32 are formed to provide a generally egg-shaped configuration as shown in FIG. 7 when inflated and providing a crescent-shaped configuration when deflated as also shown in dotted lines in FIG. 7. The interior of the balloon 81 is in communication with the balloon inflation lumen 77. Radiopaque markers 83 and 84 are provided on opposite ends of the balloon.

Still another embodiment of a low profile balloon catheter incorporating the present invention is shown in FIGS. 8 through 11 in which a low profile balloon catheter 91 is shown consisting of a flexible elongate tubular member 92 having a distal extremity 93 which is provided with a guide wire lumen 94 on one side and first and second balloon inflation lumens 96 and 97.

First and second balloons 101 and 102 are formed on the distal extremity 93 and as shown are staggered or in other words are offset in longitudinally spaced-apart positions axially of the flexible elongate tubular member 92. As shown, the balloon 101 can be a smaller balloon whereas the balloon 102 can be a larger balloon. These balloons 101 and 102 can be formed by the same molding techniques hereinbefore described. Both of the balloons are offset eccentrically in the same direction from the guide wire lumen 94 and are in communication respectively with the balloon inflation lumen 96 and the balloon inflation lumen 97. Radiopaque markers 106 and 107; 108 and 109 of the type hereinbefore described are provided one at each end of the balloons 102 and 101 respectively.

Operation and use of the low profile balloon catheter 91 is very similar to that hereinbefore described. The balloons 101 and 102 have generally an egg-shaped configuration or oval-shaped configuration as shown in FIGS. 10 and 11 when inflated. Typically in use, the smaller balloon 101 would be advanced into the stenosis and inflated and deflated to increase the size of the flow passageway through the stenosis. If a still larger flow passageway is desired in the stenosis, the smaller balloon 101 can be deflated and the catheter 91 moved distally to move the balloon 102 into registration with the stenosis after which it can be inflated and deflated to increase the size of the flow passageway through the stenosis. Thereafter, the balloons 101 and 102 can be deflated and the catheter 91 removed in the manner similar to that hereinbefore described.

Another embodiment of a low profile balloon catheter incorporating the present invention is shown in FIGS. 12–14 in the form of a low profile balloon catheter 111 consisting of a flexible elongate tubular member 112 which has a distal extremity 113 having a guide wire lumen 114 and first and second balloon inflation lumens 116 and 117 therein. As shown in FIG. 12, the guide wire lumen is generally centrally disposed with the balloon inflation lumens 116 and 117 being offset eccentrically with respect to and on opposite sides of the guide wire lumen 114.

First and second balloons 121 and 122 are formed in the distal extremity with the balloons being staggered as shown in FIG. 8 but being offset in opposite directions from that shown in FIG. 8. However, if desired, the two balloons 121 and 122 can be generally aligned as shown in dotted lines in FIG. 12 so that the balloon 121 is offset in the opposite direction from the balloon 122 if that arrangement is desired. The balloons 121 and 122 are formed in the same manner as hereinbefore described and when inflated have generally egg-shaped configurations as shown in FIGS. 13 and 14 and when deflated generally have crescent-shaped configurations. Radiopaque markers 124, 126, 127 and 128 can be provided on the distal extremity 113, one at each end of the balloons 121 and 122.

Operation and use of the low profile dilatation catheter 111 as shown in FIGS. 12—14 is very similar to that hereinbefore described. The balloons 121 and 122 can be advanced sequentially into the stenosis and inflated and deflated. If the balloons 121 and 122 are offset with respect to each other, the small balloon 121 can be inflated first followed by the second balloon 122 and thereafter by inflation of both balloons 121 and 122 simultaneously to provide a combined profile of a larger diameter. For example each of the balloons 121 and 122 each having a diameter of 2 mm can provide a combined profile of approximately 4 mm. After the desired enlargement of the flow passageway through the stenosis has been accomplished, the balloons 121 and 122 can be deflated and the catheter 111 removed in the manner hereinbefore described for the other catheters.

From the foregoing, it can be seen that there has been provided a low profile balloon catheter that makes it possible to achieve very low profiles. One or more balloons can be provided on the same catheter making it possible to readily achieve different balloon sizes permitting desired enlargements of flow passage ways through stenoses without removal of the guide wire. The balloons, since they can be constructed of the same material of which the catheter itself is formed, can be formed of a single material greatly aiding the manufacture of balloon catheters at low cost. The construction also lends itself to rapid exchange catheters in which the guide wire can be brought out through an opening (not shown) just proximal of the most proximal balloon provided on the balloon catheter. It should be appreciated that although single and double balloons have been provided on the low profile catheters of the present invention additional balloons can be provided on the distal extremity of the catheter with the corresponding number of balloon inflation lumens being carried by the catheter.

We claim:

1. A low profile catheter comprising a flexible elongate tubular member with a smooth outer surface and having proximal and distal extremities, said flexible elongate tubular member having a guide wire lumen and at least first and second balloon inflation lumens extending from the proximal extremity to the distal extremity, said first and second balloon inflation lumens being offset eccentrically with respect to said guide wire lumen, first and second inflatable balloons having proximal and distal extremities carried by the distal extremity of the flexible elongate tubular member and having respectively first and second interiors in communication, respectively, with said first and second balloon inflation lumens, at least one of said first and second inflatable balloons having a wall thickness which decreases in a direction away from the guide wire, said first and second inflatable balloons being formed of the same material as the flexible elongate tubular member with smooth transitions between the proximal and distal extremities of the first and second balloons and the smooth outer surface of the flexible elongate tubular member so there are no discontinuities at the proximal and distal extremities of the first and second inflatable balloons and the flexible elongate tubular member.

2. A low profile catheter as in claim 1 wherein one of said first and second inflatable balloons has a size which is different from the size of the other of the first and second inflatable balloons.

3. A low profile catheter as in claim 1 wherein said first and second inflatable balloons are offset from each other longitudinally of the flexible elongate tubular member.

4. A low profile catheter as in claim 1 wherein said first and second inflatable balloons are mounted eccentrically in opposite directions from each other to provide a combined profile of larger diameter.

5. A low profile catheter as in claim 1 wherein said first and second inflatable balloons have an egg-shaped configuration when inflated and a crescent-shaped configuration when deflated.

6. A method of manufacture for providing a low profile balloon catheter by the use of first and second molds and utilizing a flexible elongate tubular member formed of plastic and having proximal and distal extremities and a smooth outer surface and having a guide wire lumen and first and second balloon inflation lumens therein, said guide wire lumen being offset to one side of the flexible elongate tubular member comprising placing a mandrel in the guide wire lumen in the distal extremity of the flexible elongate tubular member, sealing off the first and second balloon inflation lumens, placing the distal extremity of the flexible elongate tubular member in the first mold having a diameter and length suitable for forming the first balloon and positioned so that the balloon will be formed eccentrically with respect to the guide wire lumen, heating the distal extremity of the flexible elongate tubular member and tensioning the same and introducing a fluid into the balloon inflation lumen to supply fluid under pressure into a portion of the flexible elongate tubular member within the mold to cause the plastic material to expand outwardly and thin out in an eccentric manner to form the first balloon and carrying with it the plastic which is to be utilized for forming the second balloon, removing the first balloon from the first mold and permitting the first balloon to cool, placing the distal extremity of the flexible elongate tubular member in the second mold having a size and shape desired for the second balloon, supplying a fluid to the second balloon inflation lumen to cause formation of a second balloon by causing the plastic forming the second balloon inflation lumen to expand eccentrically and to thin out to form the second balloon in the second mold and removing the second balloon from the second mold and permitting the second balloon to cool to thereby provide a low profile balloon catheter having first and second molded balloons having proximal and distal extremities with smooth transitions being formed between the proximal and distal extremities of the first and second balloons and the smooth outer surface of the flexible elongate tubular member.

\* \* \* \* \*